(12) United States Patent
Swaile et al.

(10) Patent No.: US 7,235,229 B2
(45) Date of Patent: Jun. 26, 2007

(54) CLEAR, STABLE, DRY-AND-NON-STICKY ANTIPERSPIRANT HAVING A SELECT GROUP OF POLAR SILICONE EMOLLIENTS

(75) Inventors: David Frederick Swaile, Cincinnati, OH (US); Amy Michelle Capretta, Cincinnati, OH (US); Heidi Marie Van Dort, Sanford, MI (US); Donald Anthony Kadlec, Midland, MI (US)

(73) Assignee: The Procter & Gamble Company, Cincinnati, OH (US)

( * ) Notice: Subject to any disclaimer, the term of this patent is extended or adjusted under 35 U.S.C. 154(b) by 568 days.

(21) Appl. No.: 10/715,654

(22) Filed: Nov. 18, 2003

(65) Prior Publication Data

US 2004/0247546 A1 Dec. 9, 2004

Related U.S. Application Data

(60) Provisional application No. 60/428,330, filed on Nov. 22, 2002.

(51) Int. Cl.
*A61Q 15/00* (2006.01)
*A61K 8/00* (2006.01)
*A61K 8/02* (2006.01)

(52) U.S. Cl. ............................ 424/65; 424/66; 424/68; 424/400; 424/401

(58) Field of Classification Search ................. 424/65, 424/66, 68, 400, 401
See application file for complete search history.

(56) References Cited

U.S. PATENT DOCUMENTS

| 4,053,581 | A | 10/1977 | Pader et al. |
| 5,084,577 | A | 1/1992 | Bolich, Jr. |
| 5,531,986 | A | 7/1996 | Shevade et al. |
| 5,968,489 | A | 10/1999 | Swaile et al. |
| 6,485,715 | B1 | 11/2002 | Smith et al. |
| 6,524,562 | B2 * | 2/2003 | Guskey ........................ 424/65 |
| 6,555,099 | B2 * | 4/2003 | Guskey et al. ................. 424/65 |

* cited by examiner

*Primary Examiner*—Shelley A. Dodson
(74) *Attorney, Agent, or Firm*—Vladamir Vitenberg; Andrew J. Hagerty; Tara M. Rosnell

(57) ABSTRACT

A clear, stable, dry-and-non-sticky feeling antiperspirant having an antiperspirant active, a solvent, and a polar silicone emollient. The antiperspirant active is solubilized in the solvent. The polar silicone emollient has an OH group or polyether or mixture thereof. The polyether has an average length of 6 or less of ethylene oxide, propylene oxide or butylenes oxide groups or mixtures thereof. The polar silicone emollient has a chain of dimethyl siloxane groups ranging in an average total length of 8 to 40 silicone atoms. The polar silicone emollient has a linker which is a hydrocarbon chain of 1 to 8 carbons in average length. The polar silicone emollient represents from about 1% to about 95%, more specifically from about 5% to about 70%, even more specifically from about 10% to about 40% by weight of the antiperspirant. The antiperspirant may be contained in a pressurized or non-pressurized container.

16 Claims, No Drawings

CLEAR, STABLE, DRY-AND-NON-STICKY ANTIPERSPIRANT HAVING A SELECT GROUP OF POLAR SILICONE EMOLLIENTS

CROSS-REFERENCE TO RELATED APPLICATION

This application claims the benefit of U.S. Provisional Application No. 60/428,330, filed Nov. 22, 2002.

TECHNICAL FIELD

The present invention relates to a clear, stable, dry-and-non-sticky antiperspirant composition having a select group of polar silicone emollients. The composition may be based on a solution of an AP active and a select group of polar silicone emollients. Additionally, the composition may be an anhydrous antiperspirant product.

BACKGROUND OF THE INVENTION

Clear, stable, dry-and-non-sticky antiperspirant (hereinafter AP) products have long been desired by consumers. Commercially available products today do not meet all of these four consumer desires. For example, water based clear AP products (e.g., simple aqueous solutions of active ingredients and water in silicone emulsions) generally feel wet during application and for a significant period of time thereafter. Another example, clear stick products (e.g., based on active dissolved in propylene glycol and Milithix thickeners) typically feel drier but are still too sticky to achieve broad consumer acceptance.

One known formulation approach for making clear, stable, dry-and-non-sticky feeling AP products is to combine a non-aqueous solution of AP active with a dry-feeling, low viscosity, non-polar silicone emollient. The silicone emollient will reduce the sticky feel of the active solution and impart a dry, lubricous feel to the product. However, use of this approach has been limited because of the incompatibility of the polar, non-aqueous solvents (e.g., diol) used to make solutions of antiperspirant actives and the non-polar silicone emollients.

There have been several ways to overcome this incompatibility presented in the literature. For example, U.S. Pat. No. 4,053,581 discloses the dissolving of an AP active and a non-polar silicone emollient (e.g., cyclomethicone) into an anhydrous ethanol. Another example, U.S. Pat. No. 6,485,715, discloses a method of dissolving an AP active in a long chain diol, and then using dimethyl ether as a propellant and coupler for combining the solubilized AP active and a non-polar silicone emollient. U.S. Pat. No. 5,968,489 discloses a method of using a polar silicone emollient (e.g., dimethiconol) as a coupler between a solubilized AP active (e.g., dissolved in a long chain diol) and a non-polar silicone emollient (e.g., cyclomethicone).

In an attempt to improve the method disclosed in U.S. Pat. No. 5,968,489, one skilled in the art might try using an alternative class of polar silicone emollients in place of dimethiconol. For instance, U.S. Pat. No. 5,084,577 discloses polar silicone emollients that would be sufficiently polar to be compatible with the solubilized AP active.

In another attempt to improve the method disclosed in U.S. Pat. No. 5,968,489, one skilled in the art might try using yet another alternative class of polar silicone emollients in place of dimethiconol, for instance, dimethicone copolyols. The term dimethicone copolyols describes a class of materials that comprise a silicone chain with attached polar side chains that are typically made of polymers of polyethylene, polypropylene, polybutylene or mixtures thereof. Dimethicone copolyols have a wide range of molecular weights, viscosities, and polarities thus making this class of compounds useful as surfactants, compatiblizers, and solvents in a wide variety of consumer products ranging from cosmetics to automotive waxes. However, one skilled in the art can not merely substitute a dimethicone copolyol for dimethiconol. In fact, doing so requires more than routine experimentation; such will be exemplified herein.

What is needed is a clear, stable, dry-and-non-sticky feeling anhydrous antiperspirant product based on a solution of an AP active and a select group of polar silicone emollients.

SUMMARY OF THE INVENTION

The present invention is directed to a clear, stable, dry-and-non-sticky feeling antiperspirant having an antiperspirant active, a solvent, and a polar silicone emollient. The antiperspirant active is solubilized in the solvent. The polar silicone emollient has an OH group or polyether or mixture thereof. The polyether has an average length of 6 or less of ethylene oxide, propylene oxide or butylenes oxide groups or mixtures thereof. The polar silicone emollient has a chain of dimethyl siloxane groups ranging in an average total length of 8 to 40 silicone atoms. The polar silicone emollient has a linker which is a hydrocarbon chain of 1 to 8 carbons in average length. The polar silicone emollient represents from about 1% to about 95%, more specifically from about 5% to about 70%, and even more specifically from about 10% to about 40% by weight of the antiperspirant. The antiperspirant may be contained in a pressurized or non-pressurized container.

DETAILED DESCRIPTION OF THE INVENTION

The clear, stable, dry-and-non-sticky feeling antiperspirant compositions of the present invention comprise an antiperspirant active in a cosmetically acceptable solvent and a polar silicone emollient with the general structure:

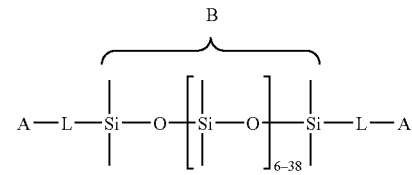

wherein
  A is an OH group or polyether or mixture thereof; wherein said polyether has an average length of 6 or less of ethylene oxide, propylene oxide or butylenes oxide groups or mixtures thereof;
  B is a chain of dimethyl siloxane groups ranging in an average total length of 8 to 40 silicone atoms; and
  L is a linker between A and B, wherein said linker is a hydrocarbon chain of 1 to 8 carbons in average length.

These and other essential elements or limitations of the clear, stable, dry-and-non-sticky feeling antiperspirant compositions of the present invention are described in detail hereinafter.

The term "anhydrous" as used herein, unless otherwise specified, refers to those compositions or materials containing less than about 5%, specifically less than about 3%, more specifically less than about 1%, and even more specifically zero percent, by weight of free or added water.

The term "ambient conditions" as used herein refers to surrounding conditions at about one atmosphere of pressure, at about 50% relative humidity, and at about 25° C.

The term "stable" as used herein refers to a product that does not show visible discoloration, hazing, or phase separation upon storage in a sealed container at 49° C. for 4 weeks.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The antiperspirant compositions of the present invention can comprise, consist of, or consist essentially of the essential elements and limitations of the invention described herein, as well as any additional or optional ingredients, components, or limitations described herein or otherwise useful in antiperspirant applications.

Polar Silicone Emollient

The clear, stable, dry-and-non-sticky feeling antiperspirant composition of the present invention comprises selected polar silicone emollients which are intended to be soluble in a solution of antiperspirant active, reduce the stickiness of the AP product and provide a lubricous feel to the consumer. The antiperspirant composition may comprise from about 1% to about 95%, more specifically from about 5% to about 70%, and even more specifically from about 10% to about 40%, by weight of the selected polar silicone emollients. The selected polar silicone emollients have the following general structure:

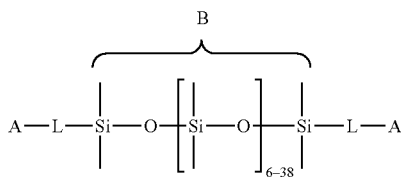

wherein

A is an OH group or polyether or mixture thereof; wherein said polyether has an average length of 6 or less of ethylene oxide, propylene oxide or butylenes oxide groups, or mixtures thereof;

B is a chain of dimethyl siloxane groups ranging in an average total length of 8 to 40 silicone atoms; and L is a linker between A and B, wherein said linker is a hydrocarbon chain of 1 to 8 carbons in average length.

These polar silicone emollients have three key structural components which are: a silicone chain, a polar terminal group (labeled A in the above diagram) and a carbon chain that links the silicone chain to the terminal polar group (labeled L in the above diagram). The silicone chain (labeled B in the above diagram) is comprised of a series of dimethyl siloxane groups ranging from about 8 to about 40 siloxane units in length. More specifically, the length is from about 10 to about 25 dimethyl siloxane units in length. It has been discovered that chain lengths shorter than about 8 dimethyl siloxane units typically do not reduce the stickiness of the active solution or provide the lubricous feel. It has also been discovered that chain lengths longer than about 40 siloxane units create an emollient that is either not soluble in the active solution or too viscous to reduce the stickiness of the active solution.

The polar terminal groups of the emollient allow the emollient to be soluble in the polar active solution. It has been discovered that the polar groups must be terminal to the silicone chain, rather than pendant to the chain, to prevent the emollient from being perceived as sticky in the product. It has also been discovered that the polar terminal groups need to be relatively small so that the emollient provides a lubricous feel to the product. To meet this requirement, one non-limiting embodiment would have the polar terminal group being an alcohol functional group. In another non-limiting embodiment, the polar terminal group is a short-chain polyether. The short-chain polyether may have an average length of 6 units or less. Additionally, the short-chain polyether may comprise an ethylene oxide (EO), propylene oxide (PO) butylenes oxide (BO) or mixtures thereof. It has been discovered that polyether chains with an average length of 7 or more units will prevent the emollient from providing a lubricous feel.

It has also been discovered that of the selected polar silicone emollients there exists a select group of dimethicone copolyols. Dimethicone copolyols are commercially available in two general structural classes: an ABA structure (e.g., polar silicone emollients described above) and a comb (or rake) structure. In comb structures, the polar groups are pendent to the silicone backbone chain. These comb structures generally have a higher mole fraction of the polar group (e.g., greater than 50%) than ABA structures (e.g., less than 50%) and as a result have a higher viscosity (e.g., greater than 300 cps as compared to less than 300 cps). Also, comb structures generally are not capable of reducing the stickiness of the antiperspirant active solution nor do they provide lubricous dry feel. For these reasons, ABA structures may be more beneficial than comb structures.

A third component of the emollient structure is a carbon chain linker which is positioned between the silicone chain (B) and the polar terminal group (A). The carbon chain linker provides the necessary acid stability to make the emollient compatible with antiperspirant active solution. More specifically, direct connection of the polar terminal group to silicone chain would result in the formation of a silanol group (if the polar terminal group was an alcohol group) or a Si—O—C bond (if the polar terminal group was a polyether), both of which have been discovered to be unstable in an acidic environment. Additionally, it has been discovered that the carbon chain linker may have a length from about 1 to about 8 carbons, and more specifically from about 3 to about 6 carbons.

Antiperspirant Active

The antiperspirant composition of the present invention comprises an antiperspirant active suitable for application to human skin. The concentration of the antiperspirant active in the composition should be sufficient to provide the finished antiperspirant product with the desired perspiration wetness and odor control. For the antiperspirant products of the present invention, the active may be dissolved in a solvent such as water, ethanol or a liquid polyol. Actives that can be solubilized in a liquid polyol solvent which has at least 3 carbon atoms and adjacent hydroxy-substituted carbon atoms at the α and β positions of the liquid polyol are believed to be beneficial.

Antiperspirant active concentrations in the antiperspirant compositions may range from about 0.1% to about 26%, more specifically from about 1% to about 20%, and even more specifically from about 2% to about 10%, by weight of the composition. All such weight percentages are calculated on an anhydrous metal salt basis exclusive of water and any complexing or buffering agent such as, for example, glycine, glycine salts.

The antiperspirant active for use in the antiperspirant compositions of the present invention may include any compound, composition or other material having antiperspirant activity. Antiperspirant actives may include astringent metallic salts, especially the inorganic and organic salts of aluminum, zirconium and zinc, as well as mixtures thereof. Particularly beneficial are believed to be salts such as aluminum halides, aluminum chlorohydrate, aluminum hydroxyhalides, zirconyl oxyhalides, zirconyl hydroxyhalides, and mixtures thereof. Aluminum salts may be beneficial for compositions that are sprayed onto the skin.

Aluminum salts for use in the antiperspirant compositions may include those that conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. One example is the aluminum chlorohydrates referred to as "5/6 basic chlorohydrate", wherein a=5, and "2/3 basic chlorohydrate" wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; and U.S. Pat. No. 4,359,456, Gosling et al., issued Nov. 16, 1982, the disclosures of which are incorporated herein by reference. Mixtures of aluminum salts are described in British Patent Specification 1,347,950, Shin et al., published Feb. 27, 1974.

Zirconium salts for use in the antiperspirant compositions include those that conform to the formula:

$$ZrO(OH)_{2-a}Cl_a \cdot xH_2O$$

wherein a is any number having a value of from 0 to about 2; x is from about 1 to about 7; and wherein a and x may both have non-integer values. Zirconium salts that additionally contain aluminum and glycine, commonly known as ZAG complexes, may be beneficially used. These ZAG complexes contain aluminum chlorhydroxide and zirconyl hydroxy chloride conforming to the above-described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978. Zirconium salts may be used in products that are rubbed directly onto the skin or are delivered via an application device that can be rubbed against the skin.

Antiperspirant actives for use in the compositions may include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, aluminum zirconium trichlorohydrate, aluminum zirconium tretrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium octachlorohydrex glycine and combinations thereof.

More specifically, the anhydrous antiperspirant compositions of the present invention comprise selected liquid polyols for solubilizing for antiperspirant active material in the composition. The antiperspirant composition comprises from about 1% to about 80%, specifically from about 2% to about 60%, and more specifically from about 3% to about 25%, by weight of the selected liquid polyols.

The liquid polyols for use in the antiperspirant composition of the present invention may have at least 3 carbon atoms and adjacent hydroxy-substituted carbon atoms at the α and β positions of the liquid polyol. Liquid polyols for use in the compositions having the following formula may be used:

$$HO-CH_2-CH(OH)-R$$

wherein R is an amide, ester, alkyl, ether or silicone-containing moiety, each moiety containing at least 1 carbon atom. The R group is an alkyl or ether group, specifically an alkyl group having from about 1 to about 10 carbon atoms, and more specifically from about 2 to about 6 carbon atoms. The liquid polyols may have either 2 or 3 hydroxyl groups in total.

The R group of the liquid polyol can be substituted or unsubstituted, branched or straight or cyclic, saturated or unsaturated. Non-limiting examples of suitable substituents include hydroxyl groups, amines, amides, esters, ethers, alkoxylate groups (e.g., ethoxylates, propoxylates, etc.) and so forth.

Non-limiting examples of the liquid polyols for use in the compositions of the present invention include 1,2-propylene glycol, glycerin, 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; and combinations thereof. Other suitable liquid polyols include glycerol ethers such as glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; and combinations thereof. Still other suitable liquid polyols include acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols such as those described in U.S. Pat. No. 5,969,172 (Nye); and combinations thereof.

Non-limiting examples of solubilized antiperspirant active for use in the antiperspirant compositions of the present invention, and methods of making the solubilized active, are described in U.S. Pat. No. 6,149,897 (Swaile); U.S. Pat. No. 6,126,928 (Swaile); and U.S. Pat. No. 5,968,489 (Swaile et al.), which descriptions are incorporated herein by reference. Other non-limiting examples of solubilized antiperspirant active and methods of making it are described in EP 0 404 533 (Smith et al.).

Carrier Liquids

The antiperspirant products of the current invention will often include a carrier liquid in addition to the polar silicone emollient to help deliver the antiperspirant active to a skin surface in a cosmetically acceptable manner. Suitable carrier liquids for use in the antiperspirant compositions of the present invention include any silicone or silicone-containing material that is known or otherwise suitable for topical application to the skin, provided that the silicone or silicone-containing material is a liquid under ambient conditions.

The concentration of the silicone liquid in the composition may range from about 0.1% to about 50%, and more specifically from about 1% to about 25% by weight of the antiperspirant composition.

Non-limiting examples of suitable volatile silicones are described in Todd et al., "Volatile Silicone Fluids for Cosmetics", Cosmetics and Toiletries, 91:27–32 (1976), which descriptions are incorporated herein by reference. Among these volatile silicones are the cyclic silicones having from about 3 to about 7, and specifically from about 5 to about 6, silicon atoms. Suitable volatile silicones include those that conform to the following formula:

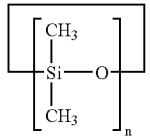

wherein n is from about 3 to about 7, specifically from about 5 to about 6, and more specifically 5. These volatile cyclic silicones generally have a viscosity value of less than about 10 centistokes as measured at 25° C. Suitable volatile silicones for use herein include, but are not limited to, Cyclomethicone D-5 (commercially available from G. E. Silicones); DC 1184, Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof. Cyclopentasiloxane can be used among the volatile silicone liquids.

Non-limiting examples of non-volatile silicone liquids for use in the antiperspirant compositions of the present invention include those that conform to either of the formulas:

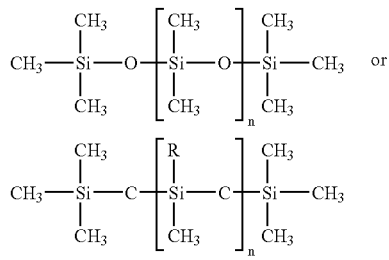

wherein n is greater than or equal to 1. These linear silicone materials will generally have viscosity values of from about 10 centistoke to about 100,000 centistoke, specifically less than about 500 centistoke, more specifically from about 10 centistoke to about 200 centistoke, even more specifically from about 10 centistoke to about 50 centistoke, as measured under ambient conditions. Non-limiting examples of non-volatile, linear silicones suitable for use in the antiperspirant compositions include but are not limited to, Dow Corning 200, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

Other silicone liquids that can be used as carrier liquids in the antiperspirant compositions of the present invention include modified or organofunctional silicone carriers such as polyalkylsiloxanes, polyalkyarylsiloxanes, cross-linked silicone elastomers, polyestersiloxanes, polyethersiloxane copolymers, polyfluorosiloxanes, polyaminosiloxanes, and combinations thereof. These modified silicone carriers are typically liquids under ambient conditions, and have a viscosity of less than about 100,000 centistokes, specifically less than about 500 centistokes, more specifically from about 1 centistoke to about 50 centistokes, and even more specifically from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Other non-silicone based carrier liquids can also be employed in the instant invention to provide different skin feel options. Some of these may also include monohydric and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Such liquid carriers may also be water-immiscible liquids under ambient conditions. Other suitable water-immiscible, polar organic liquid carriers or solvents for use in combination with the 1,2-hexanediol are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Other liquid carriers for use in the instant invention include water-miscible, polar organic liquid carriers or solvents, examples of which include short chain alcohols such as ethanol and glycol solvents such as propylene glycol, hexylene glyol, dipropylene glycol, tripropylene glycol, and so forth. Other suitable similar solvents also include polyalkoxylated carriers such as polyethylene glycols, polyproylene glycols, combinations and derivatives thereof, and so forth. Non-limiting examples of polar solvents suitable for use herein are described in U.S. Pat. No. 5,429,816.

Optional liquid carriers for use in the instant invention may also include non-polar carriers such as mineral oil, petrolatum, isohexadecane, isododecane, various hydrocarbon oils such as the ISOPAR or NORPAR series available from Exxon Corp. or PERMETHYL series available from Persperse, and the SOLTROL series available from Phillips Chemical, and any other polar or non-polar, water-miscible, organic carrier liquid or solvent known or otherwise safe and effective for topical application to human skin.

Other optional liquid carriers for use in combination with the composition include fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. Examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other examples include, but are not limited to, the polyperfluoroisopropyl ethers available from Dupont Performance Chemicals under the trade name Fluortress.® PFPE oils, and the series fluorosurfactants from Dupont Performance Chemicals under the trade name ZONYL® Fluorosurfactants.

Product Form

The antiperspirant product of the present invention may be of any form that is capable of being applied to axilla in a cosmetically acceptable manner and at an amount capable of reducing perspiration. Liquid products of the present invention could be delivered to the skin via a roll-on package, porous dome applicator, pump or aerosol package. Aerosol products of the present invention may include an appropriate propellant in the formulation to allow the product to be sprayed onto the skin surface. Gel or solid products of the present invention can be delivered from any appropriate package provided that the formulation has the requisite viscosity and or reheology for said package.

EXAMPLES

The antiperspirant compositions of the present invention include the liquid compositions shown in Examples 1–6. These compositions can be used as manufacturing intermediates to make other products, such as gels or solids, or they can be used as a topical liquid delivered from an appropriate package, e.g. roll-on applicator. Each of the exemplified compositions contains a solubilized antiperspirant active, polar silicone emollient that complies with the general structure of the current invention and were formulated by methods well known for making solubilized antiperspirant active or finished products containing solubilized active. All examples are translucent to clear and stable upon storage.

| Material | 1 % w/w | 2 % w/w | 3 % w/w | 4 % w/w | 5 % w/w | 6 % w/w |
|---|---|---|---|---|---|---|
| Aluminum chlorohydrate in 1,2 Pentanediol (a) | 20 | | | | | |
| Aluminum chlorohydrate in 1,2 Hexanediol (a) | | 10 | 33 | | 43 | |
| Aluminum Zirconium Tetrachlorohydrex glycine in 1,2 hexanediol (a) | | | | 30 | | 50 |
| KF6001 (b) | 80 | | | | | |
| KF6002 (b) | | 90 | | | | |
| DC5562 (c) | | | | | 43 | 50 |
| Silicone Polyether A (d) | | | 67 | | | |
| Silicone Polyether B (e) | | | | 45 | | |
| Cyclopentasiloxane | | | | 25 | 14 | |

(a) 20% anhydrous solution based on USP calculation;
(b) Available from Shin-Etsu Silicones of America (Akron OH);
(c) Available from Dow Corning Corp. (Midland MI);
(d) Polyether A has silicone chain length of 15 on average, a linker of 3 carbons, and poly ether terminal groups comprising 2 propylene oxide units;
(e) Polyether B has silicone chain length of 15 on average, a linker of 3 carbons, and poly ether terminal groups comprising 4 ethylene oxide units.

Pressurized Product Examples

The antiperspirant compositions of the present invention include the aerosol compositions shown in Examples 9–12. Each of the exemplified compositions contains a solubilized antiperspirant active, polar silicone emollient that complies with the general structure of the current invention and were formulated by method well known for making solubilized antiperspirant active or finished products containing solubilized active. Each of these examples was made by combining the liquid ingredients in a pressurizable container, sealing the container with a sealing valve, and then adding the propellant (A46 propellant or Dimethyl Ether) to the product through the valve. Each of these examples is clear to translucent and stable upon storage.

| Material | 7 % w/w | 8 % w/w | 9 % w/w | 10 % w/w |
|---|---|---|---|---|
| Aluminum chlorohydrate 1,2 hexanediol (a) | 30 | | 30 | |
| Aluminum chlorohydrate 1,2 pentanediol (a) | | 30 | | 30 |
| Ethanol | 8 | 0 | 4 | 0 |
| DC5562 (b) | 2 | 29 | 21.5 | 14.5 |
| DC5529 (b) | 10 | 0 | 4.5 | 4.5 |
| 10 cst Dimethicone | 9 | 0 | 0 | 10 |
| Fragrance | 1 | 1 | 1 | 1 |
| Dimethyl Ether | 10 | 40 | | 40 |
| A46 Propellant | 30 | | 40 | |

(a) 20% anhydrous solution based on USP calculation;
(b) Available from Dow Corning Corp. (Midland MI).

What is claimed is:

1. A clear, stable, dry-and-non-sticky antiperspirant composition comprising:
   (a) antiperspirant active;
   (b) solvent, said antiperspirant solubilized in said solvent; and
   (c) polar silicone emollient having the following general structure:

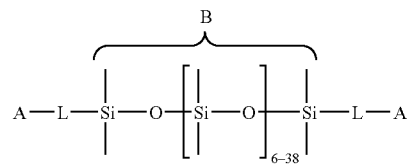

wherein
   A is an OH group or polyether or mixture thereof; wherein said polyether has an average length of 6 or less of ethylene oxide, propylene oxide or butylenes oxide groups or mixtures thereof;
   B is a chain of dimethyl siloxane groups ranging in an average total length of 8 to 40 silicone atoms; and
   L is a linker between A and B, wherein said linker is a hydrocarbon chain of 1 to 8 carbons in average length.

2. The composition of claim 1, wherein said polar silicone emollient represents from about 1% to about 95% by weight of the composition.

3. The composition of claim 1, wherein said polar silicone emollient represents from about 5% to about 70% by weight of the composition.

4. The composition of claim 1, wherein said polar silicone emollient represents from about 10% to about 40% by weight of the composition.

5. The composition of claim 1, wherein said solvent is a polyol.

6. The composition of claim 5, wherein said polyol has at least 3 carbon atoms and a hydroxyl group on each of the α and β carbon atoms, more specifically at least 4 carbon atoms and a hydroxyl group on each of the α and β carbon atoms.

7. The composition of claim 5, wherein said polyol conforms to the formula:

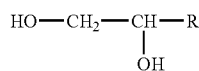

wherein R is an alkyl or ether group containing at least about 1 carbon atoms.

8. The composition of claim 7, wherein R is an alkyl group having from about 1 to about 6 carbon atoms.

9. The composition of claim 5, wherein the polyol is selected from the group consisting of 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; acetic acid glycerol ester; propanoic acid glycerol ester; butanoic acid glycerol ester; 3-methyl butanoic acid glycerol ester; 3-trimethylsily-1,2-propane diol; propylene glycol; glycerine; 1,2-hexanediol; 1,2-pentanediol; and combinations thereof.

10. The composition of claim 1 wherein the composition is anhydrous and contains less than 10% by weight of water.

11. The composition of claim 10, wherein the composition contains less than 1% by weight of water.

12. The composition of claim 1, wherein the composition is a single-phase system.

13. The composition of claim 1, wherein the composition is visibly clear or translucent.

14. The composition of claim 1, wherein the antiperspirant active represents from about 0.1% to about 35% by weight of the composition and is selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, aluminum zirconium trichlorohydrate, aluminum zirconium tretrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium octachlorohydrex glycine and combinations thereof.

15. An antiperspirant product comprising (a) the composition of claim 1 and (b) a pressurized container, wherein the composition is contained within the pressurized container.

16. An antiperspirant product comprising (a) the composition of claim 1 and (b) a non-pressurized container, wherein the composition is contained within the non-pressurized container.

* * * * *